(12) United States Patent
Ylihonko et al.

(10) Patent No.: US 6,399,583 B1
(45) Date of Patent: Jun. 4, 2002

(54) HYBRID ANTHRACYCLINES FROM GENETICALLY ENGINEERED STREPTOMYCES GALILAEUS STRAINS, PROCESS FOR PRODUCTION AND USES THEREOF

(75) Inventors: Kristiina Ylihonko, Kaarina; Juha Hakala; Tero Kunnari, both of Turku, all of (FI)

(73) Assignee: Galilaeus Oy, Piispanristi (FI)

( * ) Notice: Subject to any disclaimer, the term of this patent is extended or adjusted under 35 U.S.C. 154(b) by 0 days.

(21) Appl. No.: 09/462,671

(22) PCT Filed: May 10, 1999

(86) PCT No.: PCT/FI99/00385

§ 371 (c)(1),
(2), (4) Date: Jan. 11, 2000

(87) PCT Pub. No.: WO99/58544

PCT Pub. Date: Nov. 18, 1999

(30) Foreign Application Priority Data

May 13, 1998 (FI) .................................................. 981062

(51) Int. Cl.$^7$ .............................................. A01N 43/04
(52) U.S. Cl. ...................... 514/34; 536/16.8; 536/17.2; 536/6.4; 435/253.5; 435/252.35; 435/78
(58) Field of Search ................................. 536/6.4, 16.8, 536/17.2; 435/78, 253.5, 252.35; 514/34

(56) References Cited

U.S. PATENT DOCUMENTS 5,843,735 A   12/1998   Lee et al.

FOREIGN PATENT DOCUMENTS

WO   WO 92/16629   10/1992

OTHER PUBLICATIONS

Ylihonko et al. Production of hybrid anthracycline antibiotics by heterologous expression of Streptomyces nogalater nogalamycin biosythesis genes. (1996) 142:1965–1972, Aug. 1996.*
GenBank Accession No. AF187532 (1999) (first page only), Oct. 1999.*
GenBank Accession No. U10405 (1994) (first page only), Jun. 1994.*
Niemi et al. Hybrid anthracycline antibiotics: production of new anthracyclines by cloned genes from Streptomyces purpurascens in Streptomyces galilaeus. (1994) 140:1351–1358, Jun. 1994.*
Ylihonko et al. Isolation and characterization of aclacinomycin A–non–producing Streptomyces galilaeus (ATCC 31615) mutants. (1994) 140:1359–1365, Jun. 1994.*
Tero Kunnari et al., Bioorganic & Medicinal Chemistry Letters, vol. 7, No. 6, pp. 725–726, 1997.
Chemical Abstracts, vol. 126, 3762, 1997.

* cited by examiner

*Primary Examiner*—Ponnathapu Achutamurthy
*Assistant Examiner*—Kathla Kerr
(74) *Attorney, Agent, or Firm*—Crowell & Moring LLP (57) ABSTRACT

The present invention relates to novel hybrid anthracyclines generated by cloning of fused genes in a mutated *Streptomyces galilaeus* strain DSM 11638. Said strain was obtained by mutagenization of the *S. galilaeus* wild type (ATCC 31615). The aglycone moieties of the compounds obtained are modified alkavinones, caused by the gene products introduces into the mutant, and the sugar moieties are those derived from the host strain, i.e. rhodosamine-2-deoxyfucose-2-deoxyfucose or 2-deoxyfucose-2-deoxyfucose-2-deoxyfucose, or the disaccharide or monosaccharide forms of these.

11 Claims, 3 Drawing Sheets

HYBRID ANTHRACYCLINES FROM GENETICALLY ENGINEERED STREPTOMYCES GALILAEUS STRAINS, PROCESS FOR PRODUCTION AND USES THEREOF

FIELD OF THE INVENTION

The present invention relates to novel anthracyclines generated by cloning of fused genes in a mutated *Streptomyces galilaeus* strain. The aglycone moieties of the compounds obtained are modified aklavinones, the modifications being caused by the genes introduced into the mutant, and the sugar moieties are those derived from the host strain.

BACKGROUND OF THE INVENTION

Anthracyclines, which are mainly produced by Streptomyces species as secondary metabolites, share a great value as antitumor agents. Generally, the anthracycline molecule comprises an aglycone backbone and one or more sugar moieties attached therein. Aclacinomycins are a group of anthracyclines sharing aklavinone as the aglycone moiety and a sugar residue, as rhodosamine (Aclacinomycin T), wherein 2-deoxyfucose (Aclacinomycin S) and a third sugar, originally rhodinose, can be sequentially attached. Modifications of the third sugar residue are common. The first aclacinomycin complex consisting of Aclacinomycin A (AcmA), B (AcmB), and Y (AcmY) was first isolated from *S. galilaeus* by Oki et al., (1975). Later, aclacinomycin A, Aclarubicin, was passed through clinical trials for use in cancer chemotherapy. Research to obtain aclacinomycins with minor modifications has been carried out to find new candidates for drug development. During these studies compounds produced by the mutated *S. galilaeus* strains possessing modifications in the sugar moiety have been found (Matsuzawa et al., 1981).

The general formula of aclacinomycins (Acm) comprising aklavinone and an aminosugar, rhodosamine (Rhn) is as follows wherein R is H or a sugar residue being a mono- or a disugar-moiety.

| Anthracycline | R |
|---|---|
| AcmA | dF-CinA |
| AcmB | dF-CinB |
| AcmY | dF-Acu |
| AcmN | dF-Rho |
| AcmM | dF-Ami |

| Anthracycline | R |
|---|---|
| AcmS | dF |
| AcmT (Aklavin) | H | dF is 2-deoxyfucose, Cin is cinerulose, Acu is aculose, Rho is rhodinose, and Ami is amicetose.

In addition, aklavinone glycosides which have no aminosugar moieties have been produced by *S. galilaeus* strains obtained by mutagenesis treatment (Matsuzawa et al., 1981 and Ylihonko et al., 1994).

Aclacinomycin A, called Aclarubicin, is a unique member of aclacinomycin group used in cancer chemotheraphy. It is mainly used for leukemia. Doxorubicin, an anthracycline representing the daunomycin group, is the most widely used cytostatic antibiotic, showing activity against quite a variety of tumors. Unfortunately, the harmful side-effects such as cumulative cardiotoxicity cause the treatment by doxorubicin to be aborted despite of its effectiveness. Instead, cardiotoxicity is not a common side-effect in aclarubicin treatment. Nevertheless, the lack of activity on solid tumors limits its use mainly to leukemia and lymphomas. For this reason an optimal anthracycline for cancer treatment would possess clinical applicability similar to that of doxorubicin, whereas side-effects should rather be as those of aclarubicin, in accordance with its mode of action. Current status of cancer chemotheraphy perpetuates the need of novel molecules in order to develop new cytostatic drugs.

Matsuzawa et al. (1981) describe production of aklavinone-rhodosamine-2-deoxy-fucose-2-deoxyfucose. This aclacinomycin has been isolated from *S. galilaeus* mutant strains 7U-491 and 7N-1881 derived from the strain *S. galilaeus* ATCC 31133. As well, the strains 7U-491 and 7N-1881 produced aklavinone-Rhn-dF and, in addition, aklavinone-dF-dF (MA144 U9) has been obtained from the culture of 7N-1881.

SUMMARY OF THE INVENTION

We mutated a *Streptomyces galilaeus* wild type strain (ATCC 31615) in order to make the mutant to produce a modified anthracycline. The *S. galilaeus* mutant obtained was named as H075, and deposited under the rules of the Budapest Treaty on Jun. 30, 1997 at the Deutsche Sammlung von Mikroorganismen und Zellkulturen, Mascheroder Weg 1b, Braunschweig, Germany with the accession number DSM 11638. *S. galilaeus* H075 itself produces aklavinone-rhodosamine-2-deoxyfucose-2-deoxyfucose (H075-1a) as the major product, and minor amounts of aklavinone-dF-dF-dF (H075-1d), an anthracycline which has no aminoglycosides. H075 thereby differs from the producer strains of Matsuzawa et al. (1981), since a novel compound, aklavinone-deoxyfucose-deoxyfucose-deoxyfucose is produced as well. This mutant strain was used as the host strain to express the known genes for nogalamycin (sno) and rhodomycin (rdm) biosynthesis to produce novel hybrid anthracyclines. The sno1-3 genes derived from *S. nogalater* cause a replacement of an ethyl group at C-9 to a methyl group of aklavinone. The rdmB and E genes derived from *S. purpurascens* are responsible for hydroxylation of the positions 10 and 11, respectively, and rdmC gene product decarboxylates the position 10 in the aglycone moiety. This results in novel compounds useful in cancer chemotherapy.

A specific object of this invention is thus a process for producing new hybrid anthracyclines by transforming the genes for nogalamycin (sno) and/or rhodomycin (rdm) biosynthesis to a *S. galilaeus* strain, preferably to the H075 mutant.

The compounds produced by expressing said genes in *S. galilaeus* H075 to change the substituents at positions 9, 10 and 11 in aklavinone are included in this invention.

DETAILED DESCRIPTION OF THE INVENTION

The *S. galilaeus* mutant H075 (DSM 11638), which is used as the host for production of novel anthracyclines according to this invention is an overproducer of aklavinone glycosides. The general formula II for the said compounds is (II)

$R_4$:

(a)

(b)

(c)

(d)

(e)

wherein
$R_1 = CH_2CH_3$ or $CH_3$,
$R_2 = COOCH_3$, H or OH and
$R_3 = OH$ or H.

TABLE 1

Novel compounds of formula II

| Aglycone | Substituents | | | Glycoside |
|---|---|---|---|---|
| H075-2 | $R_1 = CH_2CH_3$ | $R_2 = OH$ | $R_3 = H$ | a,b,c,d,e |
| H075-3 | $R_1 = CH_3$ | $R_2 = COOCH_3$ | $R_3 = H$ | a,d,e |
| H075-4 | $R_1 = CH_2CH_3$ | $R_2 = COOCH_3$ | $R_3 = OH$ | a,b,c,d,e |
| H075-5 | $R_1 = CH_3$ | $R_2 = COOCH_3$ | $R_3 = OH$ | a,b,c,d,e |
| H075-6 | $R_1 = CH_3$ | $R_2 = OH$ | $R_3 = H$ | a,b,c,d,e |
| H075-7 | $R_1 = CH_3$ | $R_2 = H$ | $R_3 = H$ | a,b,c,d,e |
| H075-8 | $R_1 = CH_2CH_3$ | $R_2 = H$ | $R_3 = H$ | a,b,c,d,e |
| H075-9 | $R_1 = CH_2CH_3$ | $R_2 = H$ | $R_3 = OH$ | a,b,c,d,e |
| H075-10 | $R_1 = CH_2CH_3$ | $R_2 = OH$ | $R_3 = OH$ | a,d,e |
| H075-11 | $R_1 = CH_3$ | $R_2 = OH$ | $R_3 = OH$ | a,b,c,d,e |
| H075-12 | $R_1 = CH_3$ | $R_2 = H$ | $R_3 = OH$ | a,b,c,d,e |

In the following description the compounds are designated according to formula II above in the manner that a number is given to each aglycone based on the R-groups listed above, whereas small letters refer to sugar moieties according to formula II, a=Rhn-dF-dF; b=Rhn-dF; c=Rhn; d=dF-dF-dF; e=dF-dF. (Rhn=rhodosamine, dF=deoxyfucose).

The transformed strains obtained using *S. galilaeus* H075 as a host produce altogether 5 (sugar moiety)×11 (aglycone modifications) different anthracyclines.

The invention concerns specifically the new compounds H075-2a,b,c,d,e, H075-3a,d,e, H075-4a,b,c,d,e, H075-5a,b,c,d,e, H075-6a,b,c,d,e, H075-7a,b,c,d,e, H075-8a,b,c,d,e, H075-9a,b,c,d,e, H075-10a,d,e, H075-11a,b,c,d,e, H075-12a,b,c,d,e as given above in Table 1, and in specific the novel compounds H075-2a, -2b and -2d; H075-3d; H075-4a; H075-5e; H075-6b and -6c; H075-8a; H075-10a; and H075-11b and -11e, as defined in claim 1.

The prior known compounds related to the compounds of the present invention—as named according to the formula II—are:

H075-1a (MA144 U1, Matsuzawa et al., 1981),
H075-1b (AcmS, Oki et al., 1977),
H075-1c (Aklavin, AcmT, Streliz et al., 1956),
H075-1e (MA144 U9, Matsuzawa et al., 1981),
H075-3b (Auramycin C, Hoshino et al., 1982),
H075-3c (Auramycin D, Hoshino et al., 1982),
H075-10b (Betaclamycin S, Yoshimoto et al., 1984) and
H075-10c (Betaclamycin T, Yoshimoto et al., 1984).

The present invention enables the drug development of compounds of the formula II. According to the invention the compounds of the present study are active against the MES-SA cell line as compared with daunomycin and aclarubicin. As well, in vivo activity using P388 leukemia cells in mice was comparable with that of daunomycin. The tumor cell panel used for investigation on in vitro cytostatic activity suggests the properties relative to aclacinomycins or daunomycins depending on the substituents of the aglycone moiety. The results are encouraging to find novel pharmaceuticals for cancer treatment.

The compounds produced by the transformed strains are more hydrophilic than aclarubicin due to their chemical structures. For this reason, they resemble doxorubicin more than aclarubicin in their physicochemical properties. Doxorubicin acts on tumor cells with a mechanism distinct from that of aclarubicin. It is suggested to be an inhibitor of topoisomerase II stabilizing a drug-DNA-enzyme complex to prevent a ligation of DNA strands in double helix. This results in cell cycle arrest at phase G2. Aclarubicin is supposed to inhibit the interaction of topoisomerases with DNA, although the mechanism is not well known and the compound is found to cause the cell cycle to arrest at phase G1. The hybrid anthracyclines of the present invention were found to arrest the cell cycle at phase G1, the commitment point of chromosome replication, showing thus a mode of action similar to that of aclarubicin.

The compounds of this invention could be produced in any microbial cell able to express the genes for anthracyclines. Streptomyces species are advantageous for the purposes of this invention, and a specific embodiment comprises the use of the genetically engineered S. galilaeus H075 (DSM 11638) obtained by mutagenization of S. galilaeus ATCC 31615 wild type by NTG (N-methyl-N'-nitro-N-nitroso-guanidine).

In Streptomyces the biosynthesis of aklavinone proceeds via the polyketide pathway. Polyketide synthase (PKS) is responsible for the formation of the polyketide backbone. Three specific gene products constituting the "minimal PKS" do control the acceptance of the starter unit as well as the number of the extender units (acetate) used in the polyketide assembly. The starter unit for the aglycone biosynthesis determines the substituent at position 9 in the structure shown above. It is previously known that propionate is used as the starter in aklavinone biosynthesis wherein $R_1$ is an ethyl group. This group could be converted to a methyl group by expressing the minimal PKS genes for nogalamycin in H075, as acetate is used to start the biosynthesis pathway for nogalamycin (Ylihonko et al., 1996). The genes for nogalamycin minimal PKS (sno1-3) can be isolated from the plasmid pSY15 (DSM 9436) as a 5.4 kb DNA-fragment restricted with SacI-BglII to give pSY21. The fragment is cloned in a multicopy plasmid vector replicating in Streptomyces species.

The substituent at position 10 in aklavinone (group $R_2$) is a carbomethoxy group. This group is removed by the activity of an esterase, preferably by RdmC to produce the compounds H075-7, H075-8, H075-9 and H075-12 ($R_2$=H). RdmC is obtained by amplifying the rdmC gene by PCR (polymerase chain reaction) technique, using pJN028 as a template and by inserting the fragment amplified into pIJ486 to give pRdm52. $R_2$ is converted to a hydroxyl group by the concomitant action of RdmC and RdmB, wherein the gene product of rdmC is responsible for removing of the carbomethoxy group, while rdmB encodes a hydroxylase causing $R_2$ to be a hydroxyl group. rdmC and rdmB are cloned together to cause the conversion of a carbomethoxy group to a hydroxyl group.

11-hydroxyl group ($R_3$) could be added by the action of the rdmE gene product, a hydroxylase. The gene rdmE is obtained from pJN018 and cloned into pIJE48 to give pRdm51. The suitably fused genes cloned in the expression vector, pIJE486, cause the modifications based on the separate activities of the gene products to generate the derivatives of the compounds characteristic to the mutant strain H075 according to the present invention. Expression constructs were preferably made in S. lividans TK24 to generate large amounts of the recombinant plasmids to be introduced into S. galilaeus H039 exhibiting higher transformation frequency than the other S. galilaeus strains used. The plasmids carrying the combinations of said genes are further isolated from H039 to be introduced into S galilaeus H075 in order to produce compounds of the general formula II above. The relevant plasmids and genes are given in Table 2.

TABLE 2

The genes needed to modify aklavinone, the aglycone moiety of H075 products. The sno-genes were isolated from S. nogalater (WO 96/10581) and the rdm-genes from S. purpurascens (WO 92/16629). The designation of the compounds is according to formula II and Table 1 above.

| Compound (Table 1) | Plasmid | Genes |
| --- | --- | --- |
| H075-2 | pJN028 | rdmBC |
| H075-3 | pSY21 | sno1,2,3 |
| H075-4 | pRdm51 | rdmE |
| H075-5 | pSYR1 | sno1,2,3, rdmE |
| H075-6 | pSYR3 | sno1,2,3, rdmBC |
| H075-7 | pSYR2 | sno1,2,3, rdmC |
| H075-8 | pRdm52 | rdmC |
| H075-9 | pRdm53 | rdmC,E |
| H075-10 | pRdm54 | rdmB,C,E |
| H075-11 | pSYR4 | sno1,2,3, rdmBCE |
| H075-12 | pSYR5 | sno1,2,3, rdmC,E |

Anthracyclines representing the general formula (II) are produced by fermentation of the H075 clones, i.e. the strains carrying the plasmids listed in Table 2. The strains are H075-pJN028, H075-pSY21, H075-pSYR1, H075-pSYR2, H075-pSYR3, H075-pSYR4, H075-pSYR5, H075-pRdm51, H075-pRdm52, H075-pRdm53 and H075-pRdm54. The anthracyclines produced are isolated by extracting with organic solvents preferably using dichloromethane:methanol solution. The anthracycline of interest is separated from the mixture by column chromatography in two stages. The cytostatic activities of the purified compounds are studied using tumor cells in vitro, and in leukemia model in vivo.

In the following the detailed embodiments of the invention are described as examples of (i) carrying out the mutagenization of the *S. galilaeus* wild type (ATCC 31615), (ii) construction of the plasmids to generate the modifications for the aglycone, (iii) introduction of the plasmids into *S. galilaeus* H075 to obtain the H075 clones, (iv) isolation of the compounds produced by H075 clones, purification and identification procedures for the said compounds representing each modification caused by the genes cloned and (v) determination of cytotoxic activities in vitro and in vivo.

BRIEF DESCRIPTION OF THE DRAWINGS

FIG. 1 $^1$H-NMR-spectrum of compound H075-4a.

FIG. 2 $^{13}$C-NMR-spectrum of compound H075-4a.

EXPERIMENTAL

Materials Used
Bacterial Strains

*Streptomyces galilaeus* ATCC 31615 produces aclacinomycins. The strain was used here as the wild type for NTG-mutagenesis.

*Streptomyces galilaeus* H039 (WO 96/10581) produces aklavinone glycosides. It is used here as an intermediate strain due to a higher transformation frequency than that of H075.

*Streptomyces lividans* TK24 (WO 96/10581) does not produce anthracyclines. It is a restriction-modification-free strain used as a primary host in cloning.

Plasmids

The promoter allowing constitutive expression of the genes cloned downstream, ermE (Bibb et al., 1985) was inserted in MCS (multiple cloning site) of pIJ486 and pIJ487 (Ward et al., 1986; obtained from Prof. Hopwood, John Innes Centre, UK), generally used Streptomyces cloning vectors to give the plasmids pIJE486 or pIJE487.

Plasmid pSY15 is included in *S. lividans* DSM 9436, which plasmid contains the genes for nogalamycin chromophore derived from *S. nogalater* in the vector pIJ486. Detailed description of pSY15 is given in WO 96/10581.

pSY21 was obtained by subcloning a 3.5 kb SacI-BglII DNA-fragment from pSY15 in pIJ486 (Ylihonko et al., 1996).

EB3 is a plasmid containing a 6 kb EcoRI-BamHI-fragment of Rdm6 (WO 92/16629) inserted in pIJ486. The insert contains the genes for 11-hydroxylase, 10-demethylase, 10-hydroxylase, an aminomethylase (rdmD) and an incomplete gene for a cyclase (rdmA). The last two genes, rdmD and rdmA do not participate in aklavin-one modifications.

pJN028 is an expression construction for the genes rdmB, C,D. A 2.8 kb StyI-fragment was cloned in pIJE487 (Niemi and Mäntsälä, 1995).

pJN018 is a plasmid containing a 2.7 kb PpuMI-BamHI-fragment of EB3 cloned in pIJ487. For ligation blunt ends were used. The insert contains a complete gene for 11-hydroxylase (Niemi and Mäntsälä, 1995).

Nutrient Media and Solutions

NTG (N-methyl-N'-nitro-N-nitrosoguanidine) (SIGMA)
Thiostrepton (SIGMA) stock solution 50 µg per ml of DMSO
TSB (Tryptone-Soya Broth) Per liter: Oxoid Tryptone-Soya Broth powder 30 g.
ISP4 Bacto ISP-medium 4, Difco; 37 g/l.
E1 Per liter: Glucose 20 g, starch 20 g, Farmamedia 5 g, yeast extract 2.5 g, $K_2HPO_4 \cdot 3H_2O$ 1.3 g, $MgSO_4 \cdot 7H_2O$ 1 g, NaCl 3 g, $CaCO_3$ 3 g. Tap water is added to 1 liter and pH is adjusted to 7.4.

EXAMPLE 1

Mutagenization of *S. galilaeus* ATCC 31615 and Characterization of the Mutant Strain For mutagenization *S. galilaeus* ATCC 31615 was cultured in 50 ml of TSB medium in 250 ml Erlenmeyer flask. All flasks for mutagenesis contained a string in the bottom of the bottle to disperse mycelia during cultivation. Cultivation of the strain was carried out for two days, at 30° C., 330 rpm in a shaker. 1 ml of the culture was further inoculated to the next bottle containing 50 ml TSB and cultivation was continued for one day (30° C., 330 rpm). This younger culture was adjusted to pH 8.5 with 2% NaOH, and 800 µg/ml of NTG was added to act on the cells for 20 minutes at 37° C. The mutagenized culture of the strain was divided into two tubes and centrifuged, 300 rpm, 10 minutes. Combined pellets were used to inoculate 50 ml of TSB medium. After one day of cultivation at 30° C., 330 rpm, the whole culture was centrifuged and suspended in 10 ml of TSB medium. The titer of the cell suspension was determined by plating suitable dilutions, e.g. 1:10 on ISP4-plates. Colonies of mutagenized cultures were compared with those of the wild type and those exhibiting distinct features from the wild type were selected for further characterization.

One of the mutants was named H075. It was different from the wild type *S. galilaeus* ATCC 31615 as it appeared in deep yellow colour on the agar plate. No other features differing from the wild type were found.

The mutants selected were cultured in 60 ml of E1-medium for four days (28° C., 330 rpm). 250 µl of 1 M phosphate buffer was added to 250 µl of E1 culture and the pellet was separated from supernatant by centrifugation. The pellet was extracted by 500 µl toluene-methanol (1:1) by shaking for 1 h at room temperature. The organic phase was separated from water by adding 250 µl of phosphate buffer, and centrifuging. 10 µl sample of organic phase was applied on TLC (thin layer chromatography) plate (Kieselgel 60, Merck) and developed by toluene:ethyl acetate:methanol:formic acid (50:50:15:3). The major compound obtained from the culture of said mutant strain gave Rf-value of 0.016, whereas the major compounds of the wild type gave Rf-values of 0.11, 0.13 and 0.23, indicating Aclacinomycin A, Y and B, respectively. The total amount of aklavinone glycosides as compared with the amount of aklavinone obtained from the hydrolyzed fractions was at least five times of that produced by the wild type.

EXAMPLE 2

Construction of the Plasmids to Generate Aklavinone Modifications, and Transformation of the Plasmids to H075

2.1 General Methods

The plasmids responsible for the modifications of aklavinone, the aglycone moiety of H075 products, are listed in Table 2. The plasmids used as sources for the genes are described above in Materials used. The plasmids were isolated from relevant *S. lividans* TK24 strains, and the gene fusions were made using convenient restriction sites. Digestions were made using restriction enzymes of MBI Fermentas according to the manufacturer's instructions. For blunt end ligations the insert and the vector digested with a suitable restriction enzyme were treated with Klenow polymerase (Promega Corp. Madison, Wis.) in the presence of nucleotides to allow the filling of the 5'-sticky ends using the conditions recommended by the manufacturer. The vectors were treated with CIAP (Calf Intestinal Alkaline Phosphatase, Promega) to remove the phosphates from the 5'-end to prevent the intramolecular closure of the vector molecule. Ligations were carried out by T4 DNA Ligase (Promega) according to the instructions of the manufacturer.

2.2 Plasmid Constructions pRdm51: The gene responsible for hydroxylation of aklavinone at position 11 (rdmE) was derived from pJN018. The plasmid pJN018 was digested with BamHI restriction enzyme and ligated in BamHI-site of pIJE486. Orientation parallel with ermE promoter was checked using XhoI to give the fragments 2.2 kb and 7 kb.

pRdm52 was made by amplifying a 900 bp DNA fragment from EB3 by PCR technique. The nucleotide sequences flanking the amplified region were: 5'-ACAT-GTCCGAACGCATCGTGCCG-3' (SEQ ID NO:1) and 5'-region were: 5'-ACAT-GTCCGAACGCATCGTGCCG-3' (SEQ ID NO:1) and 5'-AGCAGCGGGCGGGAGAGACGATG-3' (SEQ ID NO:2). The restriction sites for BamHI and XbaI were introduced into the ends of the amplified region and the fragment was cloned into pIJE487 in the determined orientation.

pRdm53: pJN018 was digested with BamHI and the ends of the 2.8 kb fragment therein were blunted. The fragment was cloned in the blunt ended pRdm52 (HindIII site treated with Klenow enzyme).

pRdm54: A 6 kb DNA fragment was separated from EB3 by digestion with BglII and the fragment was cloned into the BamHI site of pIJE486. To determine the orientation of the genes for expression under the ermE promoter, MluI site was used.

pSYR1: The plasmid responsible for modifications at positions 9 and 11 in aklavinone was constructed by subcloning a DNA fragment carrying the gene for 11-hydroxylase from pJN018 in pSY21. pJN018 was digested with EcoRI and HindIII and the 5'-end was blunted by Klenow polymerase. The 2.9 kb fragment was ligated to blunted XbaI site of pSY21. The orientation of the cloned fragment was not critical as the expression of rdmE was promoted from its own promoter.

pSYR2: A 1.2 kb DNA fragment was digested from the plasmid pRdm52 by EcoRI-HindIII. The fragment was cloned into pSY21 as blunt ends.

pSYR3: A 3kb EcoRI-HindIII fragment was cloned in pSY21 as blunt end ligation.

pSYR4: pRdm54 was digested with BglII and 6.2 kb DNA fragment containing ermE promoter was ligated in pSY21 digested with XbaI and blunt ended by Klenow polymerase.

pSYR5: A 3 kb BglII fragment from pRdm53 was cloned in the blunt ended XbaI site of pSY21.

2.3 Transformation Protocols

Ligation mixtures were introduced into *S. lividans* TK24 by protoplast transformation and the plasmid was checked by miniprep method (Hopwood et al., 1985). For some plasmids the orientation was checked to be downstream from ermE promoter using suitable restriction sites.

The correct plasmid constructions were isolated from TK24 and introduced into *S. galilaeus* H039. The technique used for protoplast transformation of *S. galilaeus* strains is described in WO 96/10581. The plasmids amplified in H039 were subsequently introduced into *S. galilaeus* H075 to generate the modified reactions for the characteristic anthracyclines. 11 transformed strains, i.e. "H075 clones" were obtained, and these were named as H075-pJN028, H075-pSY21, H075-pSYR1, H075-pSYR2, H075-pSYR3, H075-pSYR4, H075-pSYR5, H075-pRdm51, H075-pRdm52, H075-pRdm53 and H075-pRdm54.

EXAMPLE 3

Production, Isolation and Purification of Compounds Accumulated by *S. galilaeus* H075 Clones

3.1 Cultural conditions for anthracycline production

Two 250 ml erlenmeyer flasks containing 60 ml of E1-medium supplemented with thiostrepton (10 $\mu$g/ml) were inoculated with the plate culture of H075 clones. After four to five days the flasks were used to inoculate Biostat fermentor containing 13 litres of E1 medium supplemented with thiostrepton (10 $\mu$g/ml), and the fermentation was carried out for four to six days (330 rpm, 30° C., aeration rate 13 l/min).

3.2 Isolation and Purification of the Anthracyclines

The fermentation broth (13 l) was adjusted to pH 7.0 with 1 M phosphate buffer, and the mycelia were separated from the broth by centrifugation. The mycelia were extracted twice with methanol (2×1 l). Methanol extracts were combined with the supernatant and the mixture was extracted twice with dichloromethane/methanol (3:1) at pH=7.5. Combined organic phases were vacuum concentrated and the viscous residue was dissolved into a chloroform:acetic acid (99:1) and loaded into a silica flash column (5 cm). The column was developed with increasing linear gradient of methanol. Pure fractions were combined, neutralized with pH=7.0 phosphate buffer and washed twice with water. Solvents were removed in rotary evaporator. The residue was dissolved in ethyl acetate and precipitated with hexane. Sedimented solids were dried under vacuum.

3.3 Structures of Novel Compounds

Figure 1:
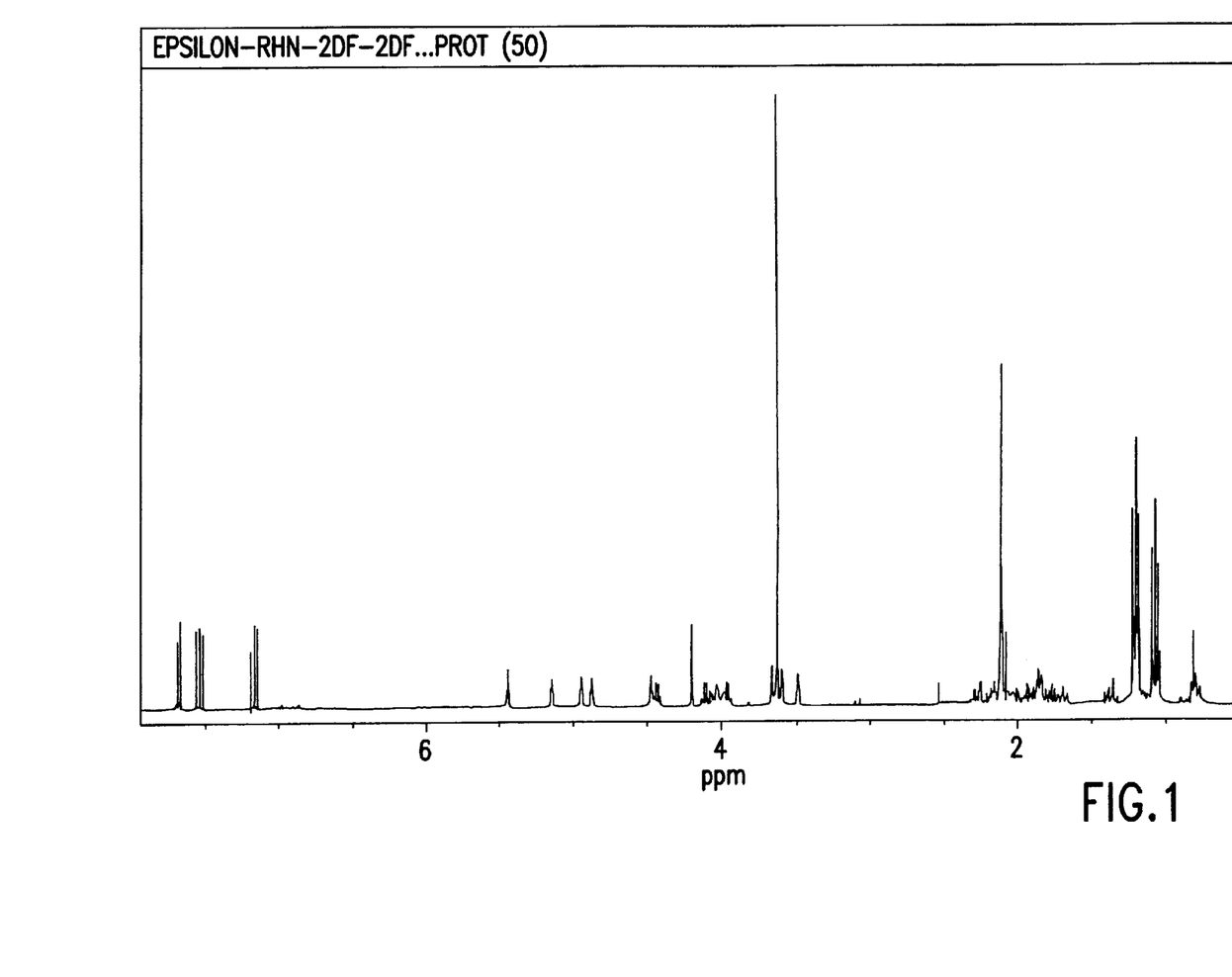
Figure 2:
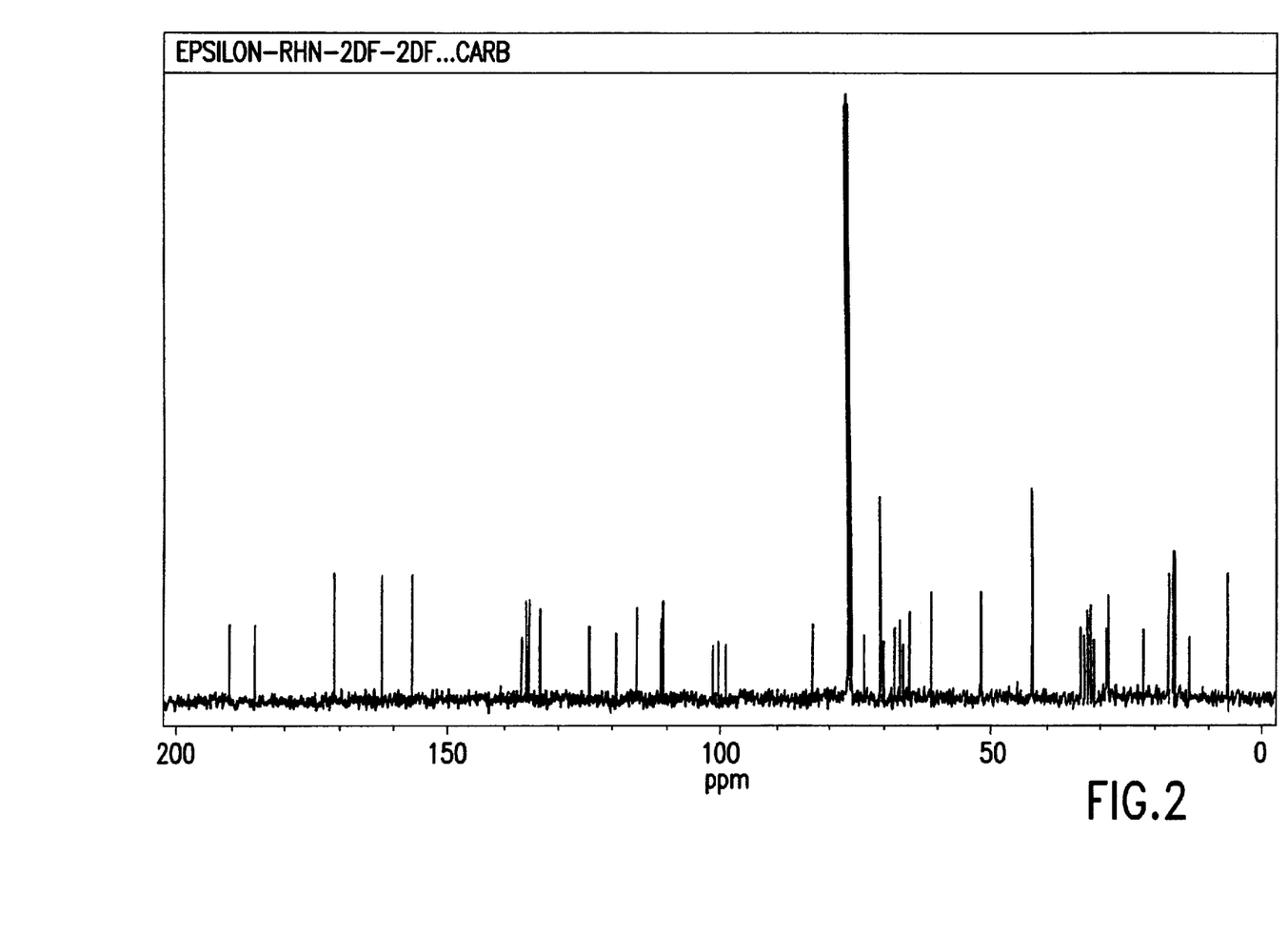
Figure 3:
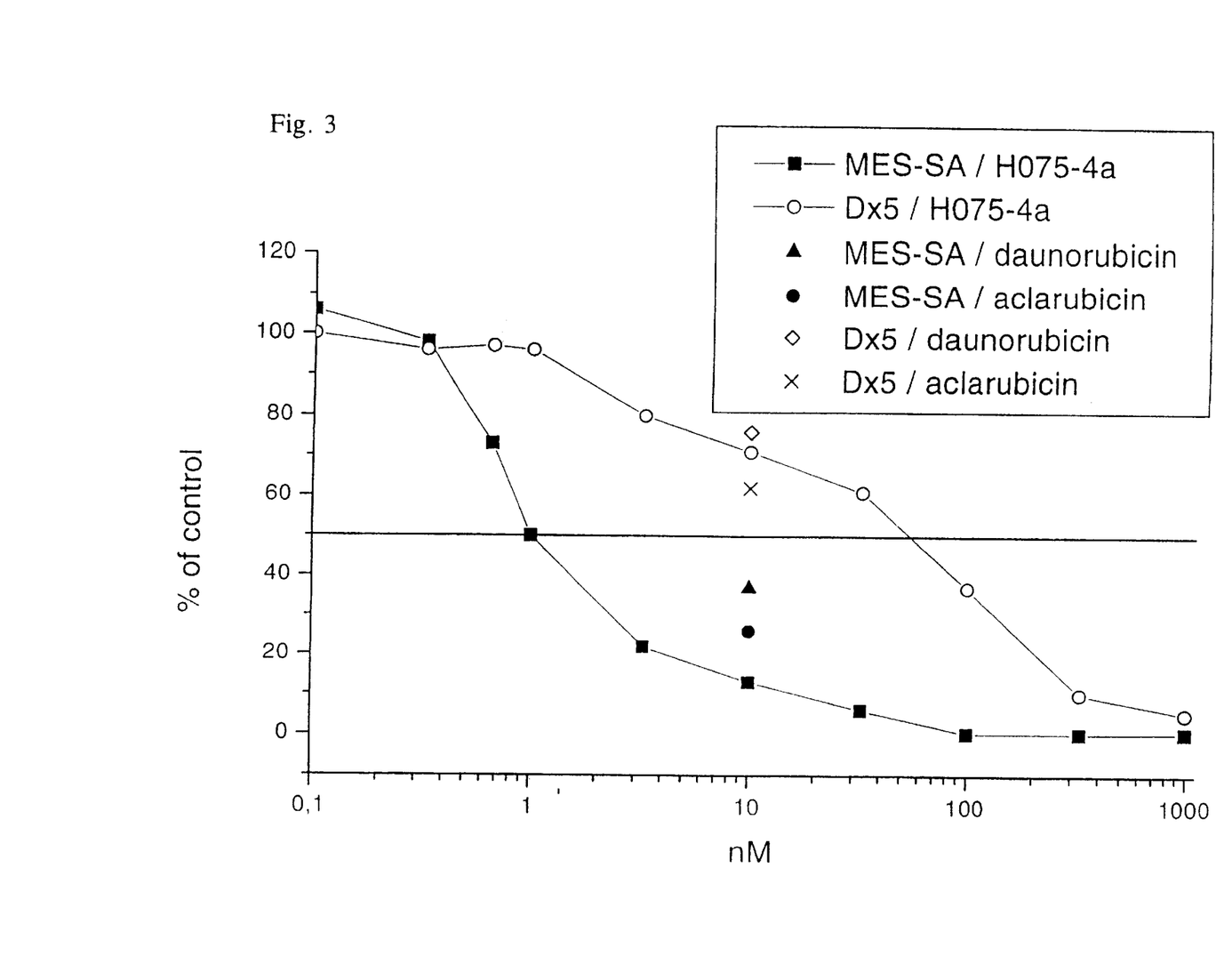
FIG. 3 Activity of compound H075-4a against MES-SA cell line.

Structures of pure anthracyclines were determined according to the data collected from NMR-spectra. Signals of NMR-data are shown in Tables 3 to 6. In FIGS. 1 and 2 the $^1$H-NMR and $^{13}$C-NMR spectra of H075-4a are given. The signals obtained were compared with those obtained from the H075 product aklavinone-Rhn-dF-dF and structural elucidation of novel compounds was deduced from the differences.

Structures of anthracyclines were deduced from NMR-data given in the Tables 3 to 6.

TABLE 3

$^{13}$C-chemical shifts of the compounds of the present invention containing an aminosugar moiety. The spectra were developed in DMSO, CHCl$_3$ or acetone. TMS was used as an internal reference.

| position | H075-1a | H075-8a | H075-2b | H075-2a | H075-4a | H075-11b | H075-6b | H075-6c | H075-10a |
|---|---|---|---|---|---|---|---|---|---|
| 1 | 120.9 | 120.0 | 119.2 | 120.1 | 119.5 | 118.8 | 119.2 | 119.6 | 118.8 |
| 2 | 137.3 | 137.1 | 136.7 | 137.2 | 136.9 | 136.4 | 136.7 | 136.9 | 136.6 |
| 3 | 124.7 | 124.6 | 124.0 | 124.7 | 124.7 | 124.0 | 124.0 | 124.2 | 124.1 |
| 4 | 162.5 | 162.4 | 161.7 | 162.4 | 162.5 | 161.8 | 161.7 | 162.1 | 157.3 |
| 4a | 115.7 | 115.8 | 115.3 | 115.9 | 116.0 | 115.4 | 115.3 | 115.1 | 115.2 |

TABLE 3-continued $^{13}C$-chemical shifts of the compounds of the present invention containing an aminosugar moiety. The spectra were developed in DMSO, $CHCl_3$ or acetone. TMS was used as an internal reference.

| position | H075-1a | H075-8a | H075-2b | H075-2a | H075-4a | H075-11b | H075-6b | H075-6c | H075-10a |
|---|---|---|---|---|---|---|---|---|---|
| 5 | 192.6 | 192.6 | 192.0 | 192.6 | 190.6 | 189.8 | 192.0 | 192.4 | 189.6 |
| 5a | 114.6 | 113.6 | 113.6 | 113.6 | 111.4 | 111.1 | 113.6 | 114.1 | 110.4 |
| 6 | 162.1 | 161.9 | 161.1 | 161.8 | 157.0 | 157.2 | 161.1 | 161.4 | 156.3 |
| 6a | 133.4 | 130.9 | 130.1 |  | 136.1 | 138.9 | 130.1 | 133.3 | 139.3 |
| 7 | 71.0 | 70.4 | 70.3 | 70.8 | 70.6 | 69.5 | 70.3 | 70.9 | 69.9 |
| 8 | 34.2 | 34.3 | 38.6 | 35.9 | 34.3 | 34.1 | 38.5 | 37.2 | 32.2 |
| 9 | 71.6 | 70.1 | 71.3 | 70.9 | 71.0 | 70.0 | 71.3 | 71.5 | 71.4 |
| 10 | 57.1 | 42.9 | 73.8 |  | 65.4 | 67.8 | 73.8 | 73.9 | 70.2 |
| 10a | 142.6 | 146.0 | 148.9 | 149.4 | 135.5 | 134.6 | 148.9 | 148.3 | 135 |
| 15 | 171.3 | — | — | — | 171.3 | — | — | — | — |
| 16 | 52.5 | — | — | — | 52.5 | — | — | — | — |
| 11 | 120.1 | 121.4 | 119.8 |  | 156.9 | 156.3 | 119.8 | 120.9 | 161.7 |
| 11a | 132.8 | 132.4 | 131.9 |  | 111.1 | 110.5 | 131.9 | 132.5 | 110.9 |
| 12 | 181.3 | 181.6 | 180.6 |  | 185.9 | 185.2 | 180.6 | 181.0 | 185.1 |
| 12a. | 131.4 | 133.5 | 133.0 |  | 133.3 | 132.8 | 133.0 | 130.1 | 132.6 |
| 13 | 32.1 | 35.1 | 22.7 |  | 33.5 | 25.3 | 22.7 | 23.6 | 28.8 |
| 14 | 6.7 | 7.4 | — |  | 6.7 | — | — | — | 6.10 |
| 1' | 99.3 | 101.1 | 99.9 | 100.6 | 101.7 | 100.6 | 99.9 | 100.2 | 100.8 |
| 2' | 29.2 | 29.2 | 28.6 |  | 29.2 | 28.6 | 28.6 | 28.1 | 29.8 |
| 3' | 61.4 | 61.5 | 60.9 |  | 61.6 | 60.9 | 60.9 | 59.4 | 61.0 |
| 3'–NMe2 | 43.2 | 43.2 | 42.7 | 43.0 | 43.2 | 42.5 | 42.7 | 41.6 | 42.8 |
| 4' | 74.0 | 74.1 | 73.3 |  | 74.2 | 73.4 | 73.3 | 65.7 | 73.4 |
| 5' | 67.2 | 68.2 | 67.6 |  | 68.5 | 67.8 | 67.6 | 66.1 | 64.8 |
| 6' | 16.8 | 17.9 | 16.5 | 17.6 | 17.8 | 17.2 | 17.4 | 16.7 | 17.2 |
| 1" | 100.8 | 99.3 | 98.6 | 98.8 | 99.4 | 98.6 | 98.6 |  | 99.8 |
| 2" | 33.7 | 37.4 | 32.2 |  | 33.0 | 32.2 | 32.3 |  | 31.8 |
| 3" | 65.4 | 65.6 | 64.9 |  | 65.7 | 64.9 | 64.9 |  | 64.8 |
| 4" | 83.8 | 83.8 | 65.9 |  | 83.6 | 70.6 | 65.9 |  | 81.2 |
| 5" | 68.3 | 66.8 | 70.6 |  | 66.9 | 66.5 | 70.6 |  | 67.7 |
| 6" | 17.0 | 17.0 | 17.4 | 16.8 | 17.0 | 16.2 | 16.5 |  | 16.6 |
| 1''' | 101.6 | 100.8 |  | 98.5 | 100.8 |  |  |  | 98.7 |
| 2''' | 33.0 | 33.0 |  |  | 32.4 |  |  |  | 33.5 |
| 3''' | 66.8 | 65.4 |  |  | 65.5 |  |  |  | 64.7 |
| 4''' | 70.6 | 71.0 |  |  | 71.1 |  |  |  |  |
| 5''' | 65.6 | 67.2 |  |  | 67.3 |  |  |  | 66.4 |
| 6''' | 17.8 | 16.8 |  | 16.9 | 16.7 |  |  |  | 16.5 |

TABLE 4

$^1H$-chemical shifts of aminoglycosides of the present invention. The spectra were run in DMSO, $CHCl_3$ or acetone. TMS was used as an internal reference.

| Position | H075-1a | H075-8a | H075-2b | H075-2a | H075-4a | H075-11b | H075-6b | H075-6c | H075-10a |
|---|---|---|---|---|---|---|---|---|---|
| 1 | 7.81, 1H, dd, 7.5, 1.1 | 7.75, 1H, dd, 7.5, 1.1 | 7.72, 1H, 7.5, 1.6 | 7.81, 1H, dd, 7.5, 1.1 | 7.67, 1H, dd, 7.5, 1.0 | 7.72, 1H, dd, 7.6, 1.6 | 7.72, 1H, dd, 7.4, 1.6 | 7.73, 1H, dd, 7.5, 1.2 | 7.77, 1H, dd, 7.6, 1.7 |
| 2 | 7.68, 1H, dd, 8.4, 7.5 | 7.61, 1H, dd, 8.4, 7.5 | 7.68, 1H, dd, 8.8, 7.5 | 7.83, 1H, dd, 8.0, 7.5 | 7.56, 1H, dd, 8.4, 7.5 | 7.61, 1H, dd, 8.4, 7.6 | 7.68, 1H, dd, 8.1, 7.4 | 7.61, 1H, dd, 8.4, 7.5 | 7.73, 1H, dd, 7.9, 7.6 |
| 3 | 7.29, 1H, dd, 8.4, 1.1 | 7.22, 1H, dd, 8.4, 1.1 | 7.26, 1H, dd, 8.1, 1.6 | 7.35, 1H, dd, 8.0, 1.6 | 7.15, 1H, dd, 8.4, 1.1 | 7.19, 1H, dd, 8.4, 1.0 | 7.26, 1H, dd, 8.1, 1.6 | 7.21, 1H, dd, 8.4, 1.2 | 7.27, 1H, dd, 7.9, 1.7 |
| 4-OH | 12.02, 1H, brs | 120.00, 1H, s | 11.95, 1H, brs | — | 11.90, 1H, brs | — | 11.95, 1H, brs | — | — |
| 6-OH | 12.66, 1H, brs | 12.57, 1H,s | 12.60, 1H. brs | — | 13.32, 1H, brs | — | 12.60, 1H, brs | — | — |

TABLE 4-continued

¹H-chemical shifts of aminoglycosides of the present invention. The spectra were run in DMSO, CHCl₃ or acetone. TMS was used as an internal reference.

| Position | H075-1a | H075-8a | H075-2b | H075-2a | H075-4a | H075-11b | H075-6b | H075-6c | H075-10a |
|---|---|---|---|---|---|---|---|---|---|
| 7 | 5.26, 1H, dd, 4.3, 1.8 | 5.16, 1H, dd, 4.2, 2.2 | 50.0, 1H, dd, 6.0, 50. | 5.09, 1H, dd, 4.7, 3.9 | 5.14, 1H, dd, 4.0, 1.9 | 50.1, 1H, dd, 4.2, 1.8 | 50.0, 1H, dd, 6.0, 5.0 | 5.02, 1H, dd, 5.5, 40. | 50.1, 1H, dd, 4.1, 3.2 |
| 8A | 2.51, 1H, dd, 14.8, 5.2 | 2.28, 1H, ddd, 14.5, 4.2, 1.6 | 2.35, 1H, dd, 14.1, 60. | 2.30, 1H, m | 2.13, 1H, dd, 15.1, 4.1 | 2.22, 1H, dd, 14.9, 4.2 | 2.36, 1H, dd, 14.1, 6.0 | 2.32, 1H, ddd, 14.5, 5.5 | 2.15, 1H, m |
| 8B | 2.30, 1H, brd, 14.8 | 2.16, 1H, d, 14.5, 2.2 | 2.05, 1H, dd. 14.1, 5.0 | 2.30, 1H, m | 2.26, 1H, dd, 15.1, 1.9 | 1.99, 1H, dd, 14.9, 1.8 | 2.05, 1H, dd, 14.1, 50. | 2.03, 1H, dd, 14.5, 40. | 2.15, 1H, m |
| 9-OH | 4.57, 1H, s | — | — | — | — | — | — | — | — |
| 10A | 1H, 4.11, s | 3.03, 1H, dd, 18.2, 1.6 | 4.50, 1H, s | 4.56, 1H, s | 4.56, 1H, s | 4.64, 1H, s | 4.50, 1H, s | 4.44, 1H, s | 4.79, 1H, s |
| 10B | — | 2.77, 1H, d, 18.2 | — | — | — | — | — | — | — |
| ester OMe | 3.69, 3H, s | — | — | — | 3.63, 3H, s | — | — | — | — |
| 11 | 7.67, 1H, s | 7.54, 1H, s | 7.90, 1H, s | 7.88, 1H, s | — | — | 7.90, 1H, s | 7.90, 1H, s | — |
| 11-OH | — | — | — | — | 12.73, 1H, brs | — | — | — | — |
| 13A | 1.74, 1H, 14.6, 7.4 | 1.57, 2H, m | 1.20, 3H, s | 1.76, 1H, m | 1.76, 1H, dq, 14.1, 7.3 | 1.35, 3H, s | 1.20, 3H, s | 1.23, 3H, s | 1.75, 1H, m |
| 13B | 1.50, 1H, dq, 14.6, 7.4 | — | — | 1.54, 1H, m | 1.38, 1H, dq, 14.1, 7.3 | — | — | — | 1.75, 1H, m |
| 14 | 1.09, 3H, t, 7.4 | 0.98, 3H, t, 7.5 | — | 1.04, 3H, t, 7,4 | 1.06, 3H, t, 7.3 | — | — | — | 1.09, 3H, t, 7.4 |
| 1' | 5.50, 1H, d, 3.2 | 5.43, 1H, d, 3.4 | 5.43, 1H, d, 20. | 5.45, 1H, d, 2.9 | 5.44, 1H, d, 2.8 | 5.38, 1H, d, 2.5 | 5.43, 1H, d, 2.5 | 5.41, 1H, d, 3.1 | 5.46, 1H, d, 30. |
| 2' | 2.10 2H, ja 1.80 cm | 1.75, 1H, m | 1.85, 2H, m | 1.88, 2H, m | 1.88, 2H, m | 1.80, 2H, m | 1.83, 2H, m | 1.73, 2H, m | 1.80, 2H, m |
| 3' | 2.09, 1H, dd, 12.0, 4.5 | 2.08, 1H, dd, 12.0, 4.5 | 2.16, 1H, m | 2.13, 1H, m | 2.07, 1H, m | 2.04, 1H, ddd, 12.9, 5.4, | 2.16, 1H, m | 2.23, 1H, m | 2.16, 1H, m |
| 3'-NMe2 | 2.16, 6H, s | 2.16, 6H, s | 2.19, 6H, s | 2.18, 6H, s | 2.11, 6H, s | 2.08, 6H, s | 2.19, 6H, s | 2.17, 6H, s | 2.19, 6H, s |
| 4' | 3.72, 1H, brs | 3.70, 1H, s | 3.73, 1H, s | 3.81, 1H, s | 3.68, 1H, s | 3.65, 1H, s | 3.73, 1H, s | 3.61, 1H, s | 3.79, 1H, s |
| 5' | 3.99, 1H, q, 6.6 | 3.98, 1H, q, 6.5 | 3.98, 1H, q, 6.6 | 4.04, 1H, q, 6.2 | 3.97, 1H, q, 6.6 | 3.95, 1H, q, 6.7 | 3.98, 1H, q, 6.6 | 3.97, 1H, dq, 6.7, 0.8 | 40.1, 1H, q, 6.6 |
| 6' | 1.27, 3H, d, 6.6 | 1.21, 3H, d, 6.5 | 1.26, 1H, d, 6.6 | 1.27, 3H. d, 6.2 | 1.20, 3H, d, 6.6 | 1.19, 3H, d, 6.7 | 1.26, 3H, d, 6.6 | 1.29, 3H, d, 6.7 | 1.29, 3H, d, 6.6 |
| 1" | 50.1, | 4.98, | 4.96, | 4.99, | 4.95, | 4.90, | 4.97, | — | 5.01, |

TABLE 4-continued $^1$H-chemical shifts of aminoglycosides of the present invention. The spectra were run in DMSO, CHCl$_3$ or acetone. TMS was used as an internal reference.

| Position | H075-1a | H075-8a | H075-2b | H075-2a | H075-4a | H075-11b | H075-6b | H075-6c | H075-10a |
|---|---|---|---|---|---|---|---|---|---|
| | 1H, d, 3.0 | 1H, d, 3.7 | 1H, d, 2.2 | 1H, d, 2.7 | 1H, d, 2.6 | 1H, d, | 1H, d, 2.2 | | 1H, d, 2.9 |
| 2" | 2.05 2H, ja 1.76 cm | 1.75, 2H, m | 1.85, 2H, m | 1.88, 2H, m | 2, 0, 2H, m | 1.80, 2H, m | 1.87, 2H, m | — | 1.80, 2H, m |
| 3" | 4.13, 1H, m | 4.06, 1H, m | 3.98, 1H, m | 3.99, 1H, s | 4.03, 1H, m | 3.94, 1H, m | 3.97, 1H, ddd, 10.3, 6.8, 30. | — | 4.03, 1H, m |
| 4" | 3.55, 1H, brs | 3.49, 1H, s | 3.52, 1H, s | 3.60, 1H, s | 3.49, 1H, s | 3.47, 1H, s | 3.52, 1H, s | — | 3.58, 1H, m |
| 5" | 4.52, 1H, q, 6.4 | 4.42, 1H, q, 6.8 | 4.42, 1H, q, 6.5 | 4.50, 1H, q, 6.5 | 4.45, 1H, q, 6.5 | 4.34, 1H, q, 6.5 | 4.42, 1H, q, 6.5 | — | 4.49, 1H, dq, 6.6, 0.7 |
| 6" | 1.16, 3H, d, 6.4 | 1.08, 3H, d, 6.8 | 1.15, 3H, d, 6.5 | 1.12, 3H, d, 6.5 | 1.08, 3H, d, 6.5 | 1.08, 3H, d, 6.5 | 1.15, 3H. d. 6.5 | 3H, d, | 3H, d, 6.6 |
| 1''' | 4.96, 1H, d, 3.3 | 4.89, 1H, d, 3.5 | — | 4.91, 1H, d, 3.2 | 4.88, 1H, d, 3.0 | — | — | — | 4.93, 1H, d, 2.9 |
| 2''' | 2.02 2H, ja 1.93 cm | 1.75, 2H, m | — | 1.88, 2H, m | 1.90, 2H, m | — | — | m | |
| 3''' | 4.13, 1H, m | 4.08, 1H, m | — | 3.99, 1H, m | 4.04, 1H, ddd, 11.6, 4.8, 2.1 | — | — | — | 4.03, 1H, m |
| 4''' | 3.68, 1H, brs | 3.62, 1H, d, 3.6 | 3.57, 1H, s 2.1 | 3.60, 1H, d, | — | — | — | 1H, m | 3.61, |
| 5''' | 4.19, 1H, q, 6.7 | 4.12, 1H, q, 7.2 | — | 4.20, 1H, dq, | 4.20, 1H, q, 6.5, 1.1 | 4.11, 1H, q, 6.6 6.6, 0.8 | — | — | 4.20, 1H, dq, |
| 6''' | 1.30, 3H, d, 6.7 | 1.23, 3H, d, 7.2 | — | 1.19, 3H, d, 6.5 | 1.22, 1H, d, 6.6 | — | — | — | 1.23, 3H, d, 6.6 |

TABLE 5

$^{13}$C-chemical shifts of the anthracyclines lacking aminosugar moieties. CHCl$_3$ was used for running the spectra. TMS was used as an internal reference.

| Position | H075-3d | H075-11d | H075-11e |
|---|---|---|---|
| 1 | 120.9 | 119.2 | 120.8 |
| 2 | 137.3 | 136.8 | 137.2 |
| 3 | 124.7 | 124.4 | 124.6 |
| 4 | 162.5 | 162.3 | 162.4 |
| 4a | 115.7 | 115.8 | 115.6 |
| 5 | 192.6 | 190.4 | 192.5 |
| 5a | 114.6 | 111.6 | 114.5 |
| 6 | 162.0 | 157.6 | 162.0 |
| 6a | 130.8 | 133.2 | 131.0 |
| 7 | 70.6 | 70.4 | 70.9 |
| 8 | 36.6 | 34.6 | 34.1 |
| 9 | 69.7 | 70.3 | 70.7 |
| 10 | 57.9 | 67.0 | 57.0 |
| 10a | 142.3 | 139.3 | 142.5 |
| 11 | 120.1 | 156.6 | 120.0 |
| 11a | 132.8 | 111.0 | 132.8 |
| 12 | 181.1 | 185.8 | 181.1 |
| 12a | 133.4 | 134.8 | 133.4 |
| 13 | 27.2 | 25.6 | 31.9 |
| 14 | — | — | 6.5 |
| 15 | 171.3 | — | 171.1 |
| 16 | 52.5 | — | 52.3 |
| 1' | 101.8 | 101.6 | 102.0 |
| 2' | 34.0 | 33.8 | 34.0 |

TABLE 5-continued $^{13}$C-chemical shifts of the anthracyclines lacking aminosugar moieties. CHCl$_3$ was used for running the spectra. TMS was used as an internal reference.

| Position | H075-3d | H075-11d | H075-11e |
|---|---|---|---|
| 3' | 65.4 | 65.0 | 67.5 |
| 4' | 82.8 | 81.8 | 82.6 |
| 5' | 67.8 | 66.9 | 65.1 |
| 6' | 17.0 | 16.8 | 16.9 |
| 1" | 100.9 | 100.5 | 100.9 |
| 2" | 34.2 | 32.6 | 33.7 |
| 3" | 65.2 | 65.0 | 67.8 |
| 4" | 82.7 | 70.6 | 82.6 |
| 5" | 67.4 | 67.3 | 65.3 |
| 6" | 17.7 | 16.6 | 16.8 |
| 1''' | 100.8 | — | 100.8 |
| 2''' | 32.7 | — | 32.6 |
| 3''' | 65.1 | — | 67.3 |
| 4''' | 70.9 | — | 71.4 |
| 5''' | 67.4 | — | 65.0 |
| 6''' | 17.7 | — | 16.7 |

TABLE 6

$^1$H-chemical shifts of the anthracyclines lacking aminosugar moieties. CHCl$_3$ was used for running the spectra. TMS was used as an internal reference.

| Position | H075-3d | H075-11e | H075-5e | H075-2d |
|---|---|---|---|---|
| 1 | 7.70, 1H, dd, 7.6, 1.1 | 7.83, 1H, dd, 7.6, 1.3 | 7.81, 1H, dd, 7.5, 1.0 | 7.74, 1H, dd, 7.5, 1.0 |
| 2 | 7.58, 1H, dd 8.4, 7.6 | 7.78, 1H, dd, 8.1, 7.6 | 7.64, 1H, dd, 8.4, 7.5 | 7.62, 1H, dd, 8.3, 7.5 |
| 3 | 7.20, 1H, dd, 8.4, 1.1 | 7.33, 1H, dd, 8.1, 1.3 | 7.25, 1H, dd, 8.4, 1.0 | 7.23, 1H, dd, 8.3, 1.0 |
| 4-OH | 11.88, 1H, s | — | 12.80, 1H, s | 11.98, 1H, s |
| 6-OH | 12.60, 1H, s | — | 13.42, 1H, s | 12.56, 1H, s |
| 7 | 5.16, 1H, dd, 4.4, 3.1 | 4.96, 1H, dd, 1.6 | 5.15, 1H, 4.2, | 4.99, 1H, d, 4.0 |
| 8A | 2.54, 1H, dd, 15.0, 4.4 | 2.23, 1H, dd | 2.28, 1H, 15.0, 4.2 | 2.20, 1H, dd, 14.5, 4.0 |
| 8B | 2.11, 1H, dd, 15.0, 3.1 | 1.99, 1H, dd, | 2.12, 1H, 1.50, 1.6 | 2.04, 1H, d, 14.5 |
| 9-OH | 4.40, 1H, s | — | — | — |
| 10A | 4.02, 1H, s | 4.60, 1H, s | 4.20, 1H, s | 4.47, 1H, s |
| 10B | — | — | — | — |
| esteri OMe | 3.64, 3H, s | — | 3.66, 3H, s | — |
| 11 | 7.55, 1H, s | — | — | 7.88, 1H, s |
| 11-OH | — | — | 12.08, 1H, s | — |
| 13A | 1.31, 3H, s | 1.35, 3H, s | 1.35, 3H, s | 1.50, 1H, m |
| 13B | — | — | — | 1.70, 1H, m |
| 14 | — | — | — | 0.96, 3H, t, 7.5 |
| 1' | 5.42, 1H, d, 3.5 | 5.36, 1H, d, 3.6 | 5.44, 1H, d, 3.5 | 5.38, 1H, d, 3.0 |
| 2'a | 1.71, 1H, ddd, 12.6, 10.2, 3.8 | 1.88, 1H, ddd, 12.6, 12.3, 3.6 | 1.88, 1H, ddd, 13.2, 12.9, 3.5 | 1.94, 1H, m |
| 2'e | 1.83, 1H, dd, 12.6, 5.1 | 1.78, 1H, dd, 12.3, 50. | 1.98, 1H, dd, 12.9, 5.2 | 1.94, 1H, m |
| 3' | 3.70, 1H, m | 3.73, 1H, m | 3.70, 1H, m | 4.05, 1H, m |
| 4' | 3.50, 1H, s | 3.65, 1H, s | 3.65, 1H, s | 3.46, 1H, s |

TABLE 6-continued $^1$H-chemical shifts of the anthracyclines lacking aminosugar moieties. CHCl$_3$ was used for running the spectra. TMS was used as an internal reference.

| Position | H075-3d | H075-11e | H075-5e | H075-2d |
|---|---|---|---|---|
| 5' | 4.08, 1H, q, 6.2 | 4.14, 1H, q, 6.5 | 4.11, 1H, q, 6.3 | 4.03, 1H, q, 6.6 |
| 6' | 1.22, 3H, d, 6.2 | 1.22, 3H, d, 6.5 | 1.23, 3H, d, 6.3 | 1.22, 3H, d, 6.6 |
| 1" | 4.88, 1H, d, 3.8 | 4.89, 1H, d, 3.2 | 4.90, 1H, d, 3.4 | 4.88, 1H, d, 3.1 |
| 2'a | 1.90, 1H, m | 1.77, 1H, ddd, 12.8, 12.3, 3.3 | 1.71, 1H, ddd, 12.8, 12.1, 3.4 | 1.94, 1H, m |
| 2'e | 1.90, 1H, m | 1.67, 1H, dd, 12.3, 4.7 | 1.86, 1H, dd, 12.5, 50. | 1.94, 1H, m |
| 3" | 4.07, 1H, m | 3.93, 1H, m | 4.10, 1H, m | 4.05, 1H, m |
| 4" | 3.54, 1H, s | 3.48, 1R, s | 3.52, 1H, s | 3.51, 1H, s |
| 5" | 4.12, 1H, q, 6.5 | 4.19, 1H, q, 6.5 | 4.11, 1H, q, 6.6 | 4.14, 1H, q, 6.4 |
| 6" | 1.20, 3H, d, 6.5 | 1.12, 3H, d, 6.5 | 1.21, 3H, d, 6.6 | 1.20, 3H, d, 6.4 |
| 1''' | 4.88, 1H, d, 3.0 | — | — | 4.88, 1H, d, 2.8 |
| 2''' | 1.88, 1H, m | — | — | 1.94, 1H, m |
| 3''' | 4.07, 1H, m | 4.05, 1H, | | m |
| 4''' | 3.60, 1H, d, 2.7 | — | 3.54, 1H, s | |
| 5''' | 4.03, 1H, q, 6.4 | — | 4.04, 1H, q, 6.5 | |
| 6''' | 1.14, 3H, d, 6.4 | — | 1.13, 3H, d, 6.5 | |

The individual changes in the molecule were seen as changes in the NMR spectra (Tables 3, 4, 5, and 6 above) as follows:

Changes in the Aglycone Part

R$_9$: The methyl at R$_9$ gives a singlet of 3 hydrogens at 1.20–1.35 ppm instead of the connected multiplet at 1.3–1.8 ppm and the triplet 1 ppm arising from the ethyl side chain.

R$_{10}$: The removal of the substituent at R$_{10}$ is seen as missing signals of C-15 and C-16 in carbon spectra and the missing singlet from the methoxy group. The decarboxylated compounds (H075-7, 8, 9 and 12) give a double doublet and a doublet arising from a CH$_2$ group while the hydroxylated compounds (H075-2, 6, 10 and 11) give a singlet of 1 hydrogen at 4.5–4.8 ppm.

R$_{11}$: Hydroxylation of position 11 is seen as a missing signal of H-11.

Changes in the Sugar Moiety

The neutral glycosides are identified because of the missing singlet of 6 H arising from the group N(CH$_3$)$_2$ of C$_3$.

The mono- and disaccharides were compared to the spectra from the trisaccharide and was found to have either a rhodosamine or a deoxyfucose as the first sugar and in all cases the second sugar was found to be a deoxyfucose as in the disaccharides.

The compounds H075-8a, -2b, -2a, -3d, -4a, -11b, -5e, -2d, -11e, -6b, -6c, and -10a were identified according these criteria to as those presented in formula II.

EXAMPLE 4

Cytotoxic Activities in vitro 4.1 In vitro Screening of Novel Compounds 4.1.1 Cell Cultures The cytotoxicities of the new anthracyclines were tested in vitro with two cell lines: human uterine sarcomas MES-SA (CRL-1976; American Type Culture Collection (ATCC), Rockville, Md., USA) and MES-SA/Dx5 (CRL-1977;

ATCC, Rockville, Md., USA). MES-SA/Dx5 has been developed by growing MES-SA cells in increasing concentrations of doxorubicin (Harker and Sikic, 1985). The selected variant is 100-fold resistant to doxorubicin and also displays a marked cross-resistance to several other cytotoxic drugs (multi drug resistance, MDR).

Monolayer cultures were grown in McCoy's 5A medium with L-glutamine (Gibco BRL) supplemented with 10% FBS (Foetal Bovine Serum, Gibco BRL). No antibiotics were added. As the resistance is stable for at least 20 passages, the MES-SA/Dx5 cells were grown without anthracycline selection (Harker and Sikic, 1985). Cells were maintained at 37° C. with 5% $CO_2$ and subcultured every 3–5 days.

4.1.2 Cytotoxicity Assays

The cytotoxicity tests were performed in 96-well microtiter plates (sterile white plates with clear bottom, Corning Costar Corporation, Cambridge, Mass., USA). The anthracyclines were pipetted into the plates in 10 µl of ethanol, pure ethanol was used for control plates. Daunorubicin and aclarubicin were used as positive controls. When the ethanol had evaporated, the cells were seeded into the plates in 100 µl of appropriate medium. The number of cells seeded per well was 2500 with MES-SA, 3000 with MES-SA/Dx5, 3000 with LL/2, 2000 with B16-F0 and B16-F1, 2000 with KLN-205 and 8000 with MLTC-1. The ATP content of the cells was measured after incubating the cells for three days at 37° C. with 5% $CO_2$.

4.1.3 Luminescence ATP Detection

The growth medium was removed by turning the plates over, and 200 µl of ATP extraction reagent, Somalyze, were added to the wells. The plates were then incubated for 30 minutes at room temperature. The ATP measurement was performed with Luminoskan luminometer (Labsystems Oy, Helsinki, Finland) at 22° C. 20 µl of ATP monitoring reagent containing luciferin and luciferase was dispensed, and an integral measurement of 10 s with 2 s lag time was performed for each well. All reagents used were supplied by Bio-Orbit Oy, Turku, Finland.

The direct luminometer output (in relative light units, RLUS) was used to calculate the cytotoxic effect. This light signal is directly proportional to the amount of ASP in a wide range (determined with Bio-Orbit ATP standard, data not shown). On the other hand, the amount of ATP is directly proportional to the amount of living cells (Kangas et al., 1984). The results are expressed as percentages of the control value of untreated cells. An $IC_{50}$ value (the drug concentration resulting to an ATP signal of 50% of the untreated control signal) was graphically estimated from the % of control vs. drug concentration plot.

4.1.4 In vitro Activities of Novel Anthracyclines

TABLE 7

$ED_{50}$ values (nM) of anthracyclines in MES-SA and MES-SA/D × 5 uterine sarcoma cells in vitro (>10000 = did not reach $ED_{50}$ at the highest concentration used, $10^{-5}$M). The first three compounds, aclarubicin, daunorubicin and H075 product (Akv-Rhn-dF-dF) were used as controls.

| Compound | MES-SA $ED_{50}$ (nM) | MES-SA/D × 5 $ED_{50}$ (nM) |
| --- | --- | --- |
| Aclarubicin | 2 | 12 |
| Daunorubicin | 8 | 220 |
| Akv-Rhn-dF-dF = H075-1a | 6 | 540 |
| H075-4a | 1 | 50 |
| H075-10a | 30 | 1300 |
| H075-11b | 60 | 3500 |
| H075-8a | 130 | >10000 |
| H075-6b | 200 | >10000 |
| H075-2b | 400 | >10000 |
| H075-11e | 800 | >10000 |
| H075-2a | 3200 | >10000 |
| H075-6c | 4200 | >10000 |
| H075-5e | 5200 | >10000 |
| H075-2d | >10000 | >10000 |
| H075-3d | >10000 | >10000 |

According to Table 7 H075-4a shows potential activity against the human cell lines studied. Its activity is similar to that of aclarubicin. All the compounds having an aminosugar (a,b,c) exhibited activity against MES-SA. Furthermore, anthracyclines possessing disaccharide dF-dF (e), showed a moderate activity against MES-SA.

4.2 Further Studies on H075-4a 4.2.1 In vitro Activities Against Mouse Cell Lines H075-4a was also tested with several mouse cell lines in vitro (all were purchased from ATCC, Rockville, Md., USA): Lewis lung carcinoma (LL/2) (CRL-1642), B16-F0 melanoma (CRL-6322), B16-F1 melanoma (CRL-6323), KLN-205 lung squamous cell carcinoma (CRL-1453) and MLTC-1 leydig cell tumor (CRL-2065) using daunomycin, aclarubicin and H075-1a (MA 144U1) as references.

All cells grew as monolayers and were cultured at 37° C. with 5% $CO_2$ according to ATCC standard instructions for each cell line: LL/2 in Dulbecco's modified Eagle's medium with 4.5 g/l glucose and 10% FCS, B16-F0 and B16-F1 in MEM (Eagle) in Earle's BSS with non-essential amino acids and 10% FCS, KLN-205 in MEM (Eagle) in Earle's BSS with non-essential amino acids and 10% FCS, MLTC-1 in RPMI 1640 with 25 mM HEPES and 10% FBS. All media were purchased from Gibco BRL, the serum was Gibco BRL Foetal Bovine Serum.

Cytotoxicity assays and ATP monitoring were carried out in the same manner as described for human cell lines.

TABLE 8

$ED_{50}$ values (nM) of H075-4a and reference compounds in different mouse cell lines in vitro.

| Compound | B16-F0 | B16-F1 | KLN-205 | LL/2 | MLTC-1 | SK-N-MC |
| --- | --- | --- | --- | --- | --- | --- |
| H075-4a | 2 | 2 | 5 | 8 | 60 | 9 |
| Aclarubicin | 3 | 4 | 12 | 5 | 70 | 9 |
| Daunorubicin | 20 | 8 | 90 | 15 | 900 | 3 |
| Akv-Rhn-dF-dF | 14 | 12 | 90 | 38 | 600 | 30 |

As deduced from Table 8, compound H075-4a is active against a variety of cell lines tested. The activities are similar to that of aclarubicin.

4.2.2 Flow Cytometry (Mode of Action of H075-4a)

L1210 mouse lymphocytic leukemia cells growing in suspension culture were maintained at exponential growth in Dulbecco's modified Eagle's medium with 4.5 g/l glucose and 10% FBS, at 37° C. with 5% $CO_2$. The experiments were started by adding the ethanol-dissolved anthracyclines, in amounts yielding to the appropriate final concentrations, to 25 $cm^2$ cell culture flasks. After the ethanol had evaporated, 5 ml of an approximately 50 000 cells per ml suspension was added to the flasks. Flow cytometric analysis was made of the original cell suspension and after one, two and three days incubation with or without the drugs.

Cells were prepared for flow cytometric DNA analysis according to the method of Vindelov et al. (1985). The analysis was performed with an Epics XL flow cytometer (Coulter Corporation, Miami, Fla.). Samples were illuminated with a 15-mV air-cooled argon ion laser (488 nm) and the fluorescence of propidium iodide was detected through 620-nm band pass filter. The number of cells in each sample was separately counted by adding an internal calibrator (50 $\mu$l of a solution containing $1 \times 10^6$ Fluoresbrite beads/ml) to 50 $\mu$l of cell suspension.

Based on the flow cytometric studies, the cell cycle phases for the cells studied could be detected. Phase G1 is the stage for RNA and protein synthesis, but not for replication. Transition from phase G1 to phase S means the initiation of replication, and the phase will last until all of the DNA has been replicated. The period from phase S up to mitosis (M) is phase G2. The hybrid anthracycline H075-4a arrested the cells in phase G1 as did aclarubicin, suggesting that the initiation of replication was prevented by this compound.

TABLE 9

Results of flow cytometry after 24 h incubation with or without anthracyclines. The cell number in the beginning was 46000 cells/ml. The percentages of cells in different cell cycle phases in the beginning are also shown.

|  | Concentration | Cells (1000/ml) | G1 (%) | G2 (%) | S + M (%) |
|---|---|---|---|---|---|
| control at 0 h |  | 46 | 32 | 12 | 56 |
| control at 24 h |  | 152 | 28 | 15 | 57 |
| H075-4a | $1 \times 10^{-8}$M | 88 | 40 | 12 | 48 |
|  | $3.3 \times 10^{-8}$M | 67 | 45 | 19 | 36 |
| Aclarubicin | $1 \times 10^{-8}$M | 101 | 43 | 14 | 43 |
|  | $3.3 \times 10^{-8}$M | 78 | 47 | 29 | 24 |
| Daunorubicin | $1 \times 10^{-8}$M | 66 | 11 | 38 | 51 |
|  | $3.3 \times 10^{-8}$M | 23 | 6 | 66 | 27 |

EXAMPLE 5

Cytotoxic Activity in vivo: Leukemia Model

P388 leukemia was maintained by serial intraperitoneal (i.p.) transplantations in DBA/2JBom female mice purchased from M & B A/S, Ry, Denmark. The animals were maintained at the facilities of Central Animal Laboratory, University of Turku. The management of the animal unit is based on and followed the guidelines: "European Convention for the protection of Vertebrate Animals used for Experimental and other Scientific Purposes, European Treaty Series No. 123 (EU No. 609/86), Official Journal of European Communities No. L 358, Strasbourg Nov. 24, 1986", and "The Statute No. 1360/90 of the Finnish Law, Helsinki Dec. 21, 1990: Asetus kokeellisiin ja muihin tieteellisiin tarkoituksiin käytettävien selkärankaisten eläinten suojelumiseksi tehdyn eurooppalaisen yleissopimuksen voimaansaattamisesta. Suomen säädoskokoelma."

The in vivo tests were started by injecting $10^6$ P388 cells suspended in Dulbecco's phosphate buffered saline i.p. in mice on day 0. Groups of 3 mice were used. The drugs were administered i.p. on day 1 on the basis of individual body weight. The control group received vehicle (10% ethanol in Dulbecco's phosphate buffered saline). The survival times of the animals were recorded and are shown in table 10. According to this data the compounds of the present invention show increased activity compared to that of daunomycin.

TABLE 10

Median survival times of mice treated with daunorubicin or H075-4a.

| Group | Treatment | Median survival days (range) |
|---|---|---|
| 1. Control | 10% ethanol i.p. | 12 (12–13) |
| 2. | daunorubicin (4 mg/kg i.p.) | 14 (14–16) |
| 3. | H075-4a (6 mg/kg i.p.) | 15 (15–16) |
| 4. | H075-4a (4 mg/kg i.p.) | 15 (13–15) |
| 5. | H075-4a (2 mg/kg i.p.) | 14 (13–16) |
| 6. | H075-4a (1 mg/kg i.p.) | 14 (13–15) |
| 7. | H075-11b (16 mg/kg i.p.) | 16 (15–19) |
| 8. | H075-11b (8 mg/kg i.p.) | 14 (13–15) |
| 9. | H075-11b (4 mg/kg i.p.) | 13 (12–13) |
| 10. | H075-10a (16 mg/kg i.p.) | 14 (14–15) |
| 11. | H075-10a (8 mg/kg i.p.) | 14 (13–15) |
| 12. | H075-10a (4 mg/kg i.p.) | 15 (14–17) |

Deposited microorganisms: The following microorganism was deposited under the rules of the Budapest Treaty at the DMSZ-Deutsche Sammlung von Mikroorganismen und Zellkulturen GmbH, Mascheroder Weg 1b, D-38124 Braunschweig, Germany

| Microorganism | Accession number | Date of deposit |
|---|---|---|
| Streptomyces galilaeus H075 | DSM 11638 | 30 June 1997 |

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

REFERENCES

Bibb, M. J., Janssen, G. R. and Ward, J. M. (1985). Cloning and analysis of the promoter region of the erythromycin resistance gene (ermE) of Streptomyces erythraeus. Gene 38, 215–226.

Harker W. G. and Sikic B. I. (1985). Multidrug (pleiotropic) resistance in doxorabicin-selected variants of the human sarcoma cell line MES-SA. Cancer Research 45, 4091–4096.

Hopwood, D. A., Bibb, M. J., Chater, K. F., Kieser, T., Bruton, C. J., Kieser, H. M., Lydiate, D. J., Smith, C. P., Ward, J. M. and Schrempf, H. (1985). Genetic manipulations of Streptomyces: a laboratory manual. The John Innes Foundation, Norwich, United Kingdom.

Hoshino, T., Tazoe, M., Nomura, S. and Fujiwara A. (1982). New anthracycline antibiotics, auramycins and sulfurmycins. II. Isolation and characterization of 10 minor components. J. Antibiot. 35, 1271–1279.

Kangas L., Grönroos M. and Nieminen A.-L. (1984). Bioluminescence of cellular ATP: a new method for evaluating cytotoxic agents in vitro. Med. Biol. 62, 338–343.

Matsuzawa, Y., Yoshimoto, A., Shibamoto, N., Tobe, H., Oki, T., Naganawa, H., Takeuchi, T., and Umezawa, H.

(1981). New anthracycline metabolites from mutant strains of *Streptomyces galilaeus* MA144-M1. II Structure of 2-hydroxyaklavinone and new aklavinone glycosides. *J. Antibiot.* 34, 959–964.

Niemi, J. and Mäntsälä, P. (1995). Nucleotide sequences and expression of genes from *Streptomyces purpurascens* that cause the production of new anthracyclines in *Streptomyces galilaeus*. *J. Bacteriol.* 177, 2942–2945.

Oki, T., Matsuzawa, Y., Yoshimoto, A., Numata, K., Kitamura, I., Hori, S., Takamatsu, A., Umezawa, H., Ishizuka, M., Naganawa, H., Suda, H., Hamada, M. and Takeuchi, T. (1975). New antitumor antibiotics, aclacinomycins A and B. *J. Antibiot.* 28, 830–834.

Oki, T., Shibamoto, N., Matsuzawa, Y., Ogasawara, T., Yoshimoto, A., Kitamura, I., Inui, T., Naganawa, H., Takeuchi, T. and Umezawa, H. (1977). Production of nineteen anthracyclic compounds by *Streptomyces galilaeus* MA144-M1. *J. Antibiot.* 30, 683–687.

Streliz, F., Flon, H., Weiss, U, and Asheshov, I. N (1956). Aklavin, an antibiotic substance with antiphage activity. *J. Bacteriol.* 72, 90–93.

Vindelov, L. L., Christensen, I. J. and Nissen, N. I. (1985). A detergent-trypsin method for the preparation of nuclei for flow cytometric DNA analysis. *Cytometry* 6, 348–356.

Ward, J. M., Janssen, G. R., Kieser, T., Bibb, M. J., Buttner, M. J. and Bibb, M. J. (1986). Construction and characterization of a series of multicopy promoter-probe plasmid vectors for Streptomyces using the aminoglycoside phosphotransferase from Tn5 as indicator. *Mol. Gen. Genet.* 203, 468–478.

Ylihonko K., Hakala J., Niemi J., Lundell J. and Mäintsälä P. (1994). Isolation and characterization of aclacinomycin A-non-producing *Streptomyces galilaeus* (ATCC 31615) mutants. *Microbiol.* 140, 1359–1365.

Ylihonko K., Tuikkanen J., Jussila S., Cong L., Mäintsälä P. (1996). A gene cluster involved in nogalamycin biosynthesis from *Streptomyces nogalater:* sequence analysis and complementation of early blocked mutations of anthracycline pathway. *Mol. Gen. Genet.* 251, 113–120.

Yoshimoto, A., Matsuzawa, Y., Ishikura, T., Sawa, T., Takeuchi, T and Umezawa, H. (1984). New anthracycline derivatives from betaclamycin A. *J. Antibiot.* 920–922.

What is claimed is:

1. Anthracycline compounds useful in cancer therapy, having the formula II, (II)

wherein
$R_1$ is $CH_2CH_3$, $R_2$ is $COOCH_3$, $R_3$ is OH and $R_4$ is Rhn-dF-dF, or
$R_1$ is $CH_3$, $R_2$ is OH, $R_3$ is OH and $R_4$ is Rhn-dF, or
$R_1$ is $CH_2CH_3$, $R_2$ is H, $R_3$ is H and $R_4$ is Rhn-dF-dF, or
$R_1$ is $CH_3$, $R_2$ is OH, $R_3$ is H and $R_4$ is Rhn-dF, or
$R_1$ is $CH_2CH_3$, $R_2$ is OH, $R_3$ is H and $R_4$ is Rhn-dF, or
$R_1$ is $CH_3$, $R_2$ is OH, $R_3$ is OH and $R_4$ is dF-dF, or
$R_1$ is $CH_2CH_3$, $R_2$ is OH, $R_3$ is H and $R_4$ is Rhn-dF-dF, or
$R_1$ is $CH_3$, $R_2$ is OH, $R_3$ is H and $R_4$ is Rhn, or
$R_1$ is $CH_3$, $R_2$ is $COOCH_3$, $R_3$ is OH and $R_4$ is dF-dF, or
$R_1$ is $CH_2CH_3$, $R_2$ is OH, $R_3$ is H and $R_4$ is dF-dF-dF, or
$R_1$ is $CH_3$, $R_2$ is $COOCH_3$, $R_3$ is H and $R_4$ is dF-dF-dF, or
$R_1$ is $CH_2CH_3$, $R_2$ is OH, $R_3$ is OH and $R_4$ is Rhn-dF-dF, and
wherein Rhn is rhodosamine and dF is deoxyfulcose.

2. The anthracycline compounds according to claim 1, wherein
$R_1$ is $CH_2CH_3$, $R_2$ is $COOCH_3$, $R_3$ is OH and $R_4$ is Rhn-dF-dF, or
$R_1$ is $CH_3$, $R_2$ is OH, $R_3$ is OH and $R_4$ is Rhn-dF, or
$R_1$ is $CH_2CH_3$, $R_2$ is OH, $R_3$ is OH and $R_4$ is Rhn-dF-dF, and
wherein Rhn is rhodosamine and dF is deoxyfucose.

SEQUENCE LISTING

<160> NUMBER OF SEQ ID NOS: 2

<210> SEQ ID NO 1
<211> LENGTH: 23
<212> TYPE: DNA
<213> ORGANISM: Streptomyces lividans

<400> SEQUENCE: 1
acatgtccga acgcatcgtg ccg         23

<210> SEQ ID NO 2
<211> LENGTH: 23
<212> TYPE: DNA
<213> ORGANISM: Streptomyces lividans

<400> SEQUENCE: 2
agcagcgggc gggagagacg atg         23

3. The derivatives of compound aklavinone-Rhn-dF-dF having the formula III (III)

wherein
R₁ is CH₃ or CH₂CH₃, R₂ is H or OH, and R₃ is H or OH, and
wherein Rhn is rhodosamine and dF is deoxyfucose.

4. A pharmaceutical composition, comprising a anthracycline compound of claim 1.

5. *Streptomyces galilaeus* H075 (DSM 11638).

6. A *Streptomyces galilaeus* strain H075 transformed with at least one of the genes or gene combinations sno1,2,3, rdmBC, sno1,2,3 rdmE, sno1,2,3 rdmC, sno1,2,3 rdmBC, sno1,2,3 rdmBCE, sno1,2,3 rdmCE, rdmE, rdmC, rdmCE, and rdmBCE.

7. A process for the production of hybrid anthracyclines comprising:
(a) transforming host cells with genes for nogalamycin and/or rhodomycin biosynthesis enabling the change of substituents of at least one of the positions 9, 10 and 11 of the aklavinone backbone,
(b) culturing the transformed host cells of (a) in conditions suitable for the expression of said genes, and
(c) recovering the hybrid anthracyclines produced;
wherein said host cell is the *Streptomyces galilaeus* host cell H075; and
wherein the genes for nogalamycin biosynthesis are selected from the group consisting of sno1, sno2, and sno3 genes from *Streptomyces nogalater* and/or the genes for rhodomycin biosynthesis are selected from the group consisting of rdmB, rdmC, and rdmE genes from *Streptomyces purpurascens*.

8. The process according to claim 7 for the production of a compound of formula II (II)

wherein R₁ is CH₂CH₃ or CH₃, R₂ is COOCH₃, H or OH, R₃ is OH or H and R₄ is Rhn-dF-dF, Rhn-dF, Rhn, dF-dF-dF, or dF-dF, wherein Rhn is rhodosamine and dF is deoxyfucose.

9. A process for the production of anthracyclines of formula II (II)

wherein R₁ is CH₂CH₃, R₂ is COOCH₃, R₃ is H and R₄ is Rhn-dF-dF, Rhn-dF, Rhn, dF-dF-dF, or dF-dF, wherein Rhn is rhodosamine and dF is deoxyfucose, comprising culturing the strain *Streptomyces galilaeus* H075 (DSM 11638) in conditions enabling the production of anthracyclines, and recovering the anthracyclines produced.

10. A method of treatment of cancer, comprising administering an effective amount of a anthracycline compound of claim 1.

11. The method of claim 10, wherein the cancer is leukemia.

* * * * *